United States Patent [19]

Lustgarten

[11] 4,141,144

[45] Feb. 27, 1979

[54] DENTAL MATERIAL AND METHOD FOR CONTROLLING TOOTH LUSTRE

[76] Inventor: Stewart J. Lustgarten, 73 Dalton Rd., Holliston, Mass. 01746

[21] Appl. No.: 762,526

[22] Filed: Jan. 26, 1977

[51] Int. Cl.$^2$ .......................... A61K 5/06; C08K 3/34
[52] U.S. Cl. ..................................... 32/15; 260/42.14; 260/42.15; 260/42.28; 260/42.52; 260/998.11
[58] Field of Search ............ 260/42.52, 998.11, 42.28, 260/42.14, 42.15; 32/15

[56] References Cited

U.S. PATENT DOCUMENTS

| | | | |
|---|---|---|---|
| 3,087,827 | 4/1963 | Klenke | 106/300 |
| 3,442,851 | 5/1969 | McManimie | 260/42.52 |
| 3,927,906 | 12/1975 | Lee | 260/42.15 |

OTHER PUBLICATIONS

Damusis, Sealants, Reinhold Pub. Corp., New York, 1967, pp. 67–69.

*Primary Examiner*—James H. Derrington
*Attorney, Agent, or Firm*—Eugene Lieberstein

[57] ABSTRACT

The dental material of the present invention comprises a polymerizable binder, a polymerization agent and an additive comprising finely divided particles of muscovite mica in a range of from about 1 to 20 percent by weight of the dental material for direct dental filling and restoration applications and in a range of from about 1 to 30 percent for cosmetically treating the surface of a tooth as a veneer or paint-on.

20 Claims, No Drawings

DENTAL MATERIAL AND METHOD FOR CONTROLLING TOOTH LUSTRE

This invention relates to an esthetic dental material for facing, restoring and filling teeth and to a method for controlling the hue and/or lustre of such material.

For esthetic reasons the treatment of anterior teeth within the oral cavity requires the consideration of factors which are not as important to the treatment of posterior teeth. One factor which is of particular concern is the ability to match the hue and lustre of th tooth being treated to adjacent teeth. For purposes of the present specification the term "hue" refers to the different shades of natural tooth enamel which are identified in accordance with common dental practice by comparison with standard shade guides provided by resin manufacturers. In contrast, the term "lustre" is defined for purposes of the present specification as a measure of the average light reflectance from a tooth surface and corresponds to the visual sensation of brightness which arises from the stimulation of the human eye in response to the illumination of the tooth. For ideal matching of teeth the hue and lustre should be equivalent under all lighting conditions. Since the reflectivity characteristics of a natural tooth increases gradually with increasing wavelength within the visible spectrum and is not uniform across the tooth surface even a close to ideal match is purely by chance. The objective is in reality a blending of the treated tooth with the natural teeth. The treatment of teeth using the dental material of the present invention may involve for example, any of the following dental operations: direct filling, fissure sealing, temporary or permanent restorations such as the formation of a crown, jacket or bridge, or as a "paint-on" to control lustre and to hide blemishes and discolorations. A "paint-on38 is defined as a thin film of dental material to be applied directly over the dental enamel of a tooth within the mouth as one would apply nail polish to a fingernail.

Current practice is to incorporate organic dyes and brighteners into dental resin composites for restorations and direct fillings in order to reproduce a shade corresponding to a particular shade guide. This is a trial and error procedure. Known pigment dyes provide optical absorption characteristics unlike natural teeth. Many are not color stable for dental applications in the mouth and almost al suffer from an inability to reproduce the translucency and lustre of natural teeth. Moreover, there is no available preblended mix which can be added to dental materials to provide control over the hue and particularly the lustre of the material with any assurance of predictability.

It is also current practice to employ clear resin monomer(s) such as a clear BIS-GMA or ethyl 2cyanoacrylate for use as a tooth glaze. Where pigments or colorants are not added, clear glazes give the tooth a glassy appearance and will not cover any blemishes or unsightly discolorations. Where a conventional pigment such as $TiO_2$ is added the material is considered too opaque for dental use.

It has been discovered in accordance with the present invention that the lustre of dental resin materials containing a polymerizable binder for use in filling, facing and restoring teeth may be controlled by the incorporation of finely divided particles of translucent muscovite mica within a preferred size range of between 1 to 50 microns. Control over lustre is achieved by varying the size distribution of mica particles within the preferred size range.

It has in addition been discovered that the optical properties of the dental material may be further enhanced providing control over hue and lustre when the uncoated translucent mica particles are combined with either titanium dioxide, zirconium dioxide or bismuth oxychloride coated mica particles within the same preferred size range. Alternatively, the coated mica particles may be combined or used separately and without uncoated mica particles. In the latter case the hue of the coated mica particles may be varied by varying the weight ratio of the coating to the mica substrate exclusive of or in addition to the control achieved by varying the particle sizes within the preferred size range and/or by varying the percentage of mica in the material.

It is therefore an object of the present invention to provide a dental material for facing, restoring and filling teeth which will provide a predetermined hue and/or lustre with a high degree of predictability.

It is a further object of the present invention to provide a method for controlling hue and/or lustre of dental resin materials containing a polymerizable monomer for use in filling, facing and restoring teeth.

Other objects and advantages of the present invention will become apparent from a consideration of the following description.

The dental material of the present invention may include any known polymerizable resinous binder, such as suitable monomers, or combination of monomers and polymers which will harden by polymerization into a nonporous solid structure. Various acrylic resin binders are commonly used in the field of dentistry for facing and restoring teeth. In addition to the binder and the polymerizing agent(s) the dental material should include an additive comprising finely divided particles of translucent muscovite mica having an average size of preferably less than about 50 microns for controlling the lustre of the dental material as will be taught hereafter. The additive should represent about 1 to about 85 percent by weight of the dental material depending upon the specific dental treatment involved and the degree of lustre of the material required.

For restoring individual teeth; as a veneer for crowns and bridges and as a paint-on for covering blemishes and discolorations, the additive may represent a significant or even the major constituent of the dental material. Alternatively, in the preparation of a direct filling composite the additive should represent only a minor constituent of the dental material. In the latter regard, although not limited thereto, the dental material should further include an inorganic filler material, in a form of finely divided particles, such as, for example: silica, glass beads, aluminum oxide, fused silica, fused or crystalline quartz or the like. The particle size of the finely divided filler particles may range from submicron to about 125 microns with the fused silica generally being in the submicron range and with the quartz and the glass beads in the micron range. When one or a combination of the foregoing filler materials is present in the dental material, the mica particles in the additive were observed to disperse homogeneously throughout the dental material and in particular formed, in combination with the filler particles, a matrix having excellent loading characteristics; viz., the interstices between larger filler particles were filled with the smaller mica particles.

Muscovite mica particles may be used by themselves as the additive or in combination with muscovite mica particles coated with titanium dioxide, zirconium dioxide and/or bismuth oxychloride or alternatively the coated particles may be used alone. Titanium dioxide is the preferred coating material for the mica particles. The coated and uncoated particles may range in size from about 1 micron to about 100 microns with a preferred range of from one to fifty microns. The control over hue and lustre of the dental material is achieved by varying the concentration of particle sizes within the preferred 50 micron range, the percent of mica in the material or alternatively by varying the weight ratio of coating to the mica or by a combination thereof. Once the hue and/or lustre is selected the dental material may be repeatedly reformulated with a degree of predictability over hue and lustre heretofore totally unattainable.

The mica particle of the present invention is a micaceous mineral of the muscovite species which is translucent and has a flake-like geometry. The flake-like mica particles are commercially available in varying average size concentration within the preferred particle size range. The flake-like particles vary from 0.05 to 3 microns in thickness and have two primary dimensions with the aforementioned preferred micron size range of 1-50 microns representing the major dimension. The preferred lower size limit of about one micron is based on the particle passing through a 325 mesh screen and approaching 400 mesh screen.

The flake-like geometry is believed to represent a significant factor in achieving the degree of control over hue and lustre of the dental material. Accordingly, although any conventional process may be used to deposit a coating of $TiO_2$, $ZrO_2$ or $BiOCl$ over the mica particles, it is important that the resulting coated particles retain the flake geometry. A typical hydrolysis process for coating a metal oxide such as titanium dioxide over mica flake particles is taught in U.S. Pat. No. 3,087,827. The thickness of the metal oxide coating is a readily controlled factor as indicated in the foregoing patent. Mica particles coated with either $TiO_2$ or bismuth oxychloride and having a flake-like geometry in varying size concentrations within the preferred range is available commercially.

It is known that coated mica particles cause light interference which can produce a spectrum of colors when struck by ordinary white light in an appropriate medium. The color produced depends upon the difference in phase, the direction in which the light travels through the medium with respect to the optic axes and the medium thickness. The color produced can be changed by varying the weight ratio between the coating, e.g., $TiO_2$ and the mica. For purposes of the present invention only the relative transparency properties of the $TiO_2$ coated mica particles is taken advantage of with the exception of reflecting the color gold because natural teeth transmits some yellow. The transparency properties provide either a white or pearly shading of the dental material with different degrees of lustre which may be varied by varying the relative weight ratio between the coating and the mica or by varying the size concentration of the particles.

The coated mica particles may be used alone or judiciously intermixed with uncoated mica particles to provide a controlled hue and lustre in a dental facing, restoration or tooth filling. For use as a paint-on without a filler additive however, no discernible hue can be readily observed. This is due to the fact that an unfilled paint-on colorless resin system is too thin having a thickness of for example only severa mils. Nonetheless the lustre of the tooth upon which the paint-on of the present invention has been applied can still be widely varied by the method of the present invention. When a filler is added to the paint-on composition with uncoated mica particles both the hue and lustre are controllable factors. It should be noted that the preference for coated mica, uncoated mica, or a combination will depend on the particular application and the selection of resin monomer, polymerizing agent and the filler if one is being added. Accordingly, although uncoated muscovite mica is of itself colorless and has a relatively low index of refraction as compared to natural teeth, it can, in the proper dental material composition, as one of the examples will hereafter substantiate, provide both hue and lustre control. This is believed attributable to its ability to diffuse light. It should also be understood that the invention does not exclude the use of conventional pigments as further additives if so desired.

The resin binder suitable for use in the present invention may include any conventional binder used in the field of dental work. The most frequently used binders include, for example, acrylic monomers or comonomers alone or in combination such as methacrylate esters, i.e. methyl methacrylate, ethyl methacrylate and the higher methacrylate esters such as n-propyl, isopropyl, n-butyl, isobutyl or glycol di-methacrylate, polymethacrylates, and/or methyl, ethyl or isopropyl cyanoacrylates. A particularly preferred binder is disclosed by Bowen in U.S. Pat. No. 3,066,112 (the disclosure of which is incorporated herein by reference). That patent discloses binder systems composed of the monomers, referred to in the art as BIS-GMA, admixed with other active monomers.

As taught in the aforementioned patent and as is well-known to those skilled in this art, "BIS-GMA" is the condensation product of two moles of methacrylic acid and the diglycidyl ether of bisphenol A or alternatively two moles of glycidyl methacrylate with one mole of bisphenol A and has the following chemical nomenclature; 2,2-bis[4-(3-methacryloxy-2-hydroxypropxy)-phenyl]-propane. A bisphenol A dimethacrylate can also be added to BIS-GMA if desired. An alternative or additional comonomer which has shown excellent adhesive characteristics to dentin is the addition reaction product of N-phenylglycine and gylcidyl methacrylate. It is pointed out in said patent that the viscosity of BIS-GMA should be reduced by the addition of a reaction diluent such as, for example, methyl methacrylate, ethylene or triethylene glycol dimethacrylate and tetraethylene glycol dimethacrylate. The diluent should comprise no more than about 20% by weight of the monomer composition in the dental material. A polymerization activator should be added to trigger the polymerization of the monomer composition. The activator used will depend upon the monomer composition selected and the desired curing time. Suitable activators are N,N-dimethyl-para-toluidine, para-tolemenesulfinic acid and N,N-dialkylanilines. The activator is generally employed in amounts varying from about 0.1 to about 2.0 weight percent based upon the weight of the resin monomer composition.

Cyanoacrylate monomers will polymerize in the presence of an activator at room temperature whereas the methacrylate group and BIS-GMA generally require the inclusion of a suitable catalyst, such as a peroxide or persulfate catalyst. An ultra violet sensitive catalyst such as methyl benzoin ether may also be used when very low concentrations of mica are used. The preferred catalyst is benzoyl peroxide. Where a catalyst is necessary it would generally be present in amounts of about 1 to about 2 percent by weight of the monomer composition exclusive of the activator.

It is desirable particularly for a BIS-GMA resin system, to treat the muscovite mica particles, both uncoated and coated with a keying agent to improve the bond between such particles and the resin and also with the filler particles, when the latter is to be incorporated into the dental material. In fact, it is recommended that the filler particles should likewise be treated with a similar keying agent. Suitable keying agents are the high performance ethylenically unsaturated organosilane compounds such as gamma-methacryloxypropyltrimethoxysilane, vinyltrichlorosilane, vinyltriethoxysilane, vinyltrimethoxysilane, vinyltriacetoxysilane and the like. An example of such treatment for the filler particles is disclosed in U.S. Pat. No. 3,066,112 using an aqueous solution of tris(2-methoxy ethoxy) vinyl silane catalyzed with sodium hydroxide in which the filler is treated. The muscovite mica particles may be similarly treated with such solution.

The dental material may be packaged for use by the dentist as a paste-liquid system, a paste-paste system or as a liquid or semi-liquid system only, particularly for application as a paint-on. The paint-on dental material need only include the resin monomer composition, polymerizing agent(s) and a suitable combination of particles of muscovite mica within the 1–50 micron range as heretofore taught. The formulaton of mica particles may be pre-blended for use with a particular monomer composition or sold along with the monomer composition exclusive of the polymerizing agent to be added prior to actual use. Some filler material may also be added. For paint-on application the mica particles can represent up to 85% by weight of the dental material depending on the resin system and the viscosity of the resin but preferably should represent no more than 30 percent. The lower limit depends upon how little lustre is desired and whether only coated mica particles are being used. At least about 1% is necessary to observe any lustre conditioning.

A typical paste-liquid is taught in the aforementioned U.S. Pat. No. 3,066,112 wherein the BIS-GMA monomer is combined with the inorganic filler to form a paste. The reactive diluent, activator and catalyst are introduced as liquids.

A paste-paste system is described in U.S. Pat. No. 3,926,906. A two part system is disclosed each containing a paste formed from dividing the binder which comprises a BIS-GMA monomer with a suitable reactive diluent such as triethylene glycol dimethacrylate and representing about 15% of the monomer into two parts indicated as part A and part B. The binder may also include submicron size filler particles such as flocculated silica to prevent settling of the paste components. To each paste a filler material is added such as fused silica, ground quartz, glass beads, or barium flouride glass beads with the filler representing about 75% of the total filling material. Part A however, contains the activator N,N-dimethyl-p-toluidine whereas Part B contains the catalyst benzoyl peroxide. This paste-paste system substantially as represented above is sold commercially under the trademark "Adaptic", a trademark of the Johnson and Johnson Corporation. The binder is colorless and the filler materials are transluent. However, the reactive diluent and the activator causes the material to become color unstable when exposed to ultraviolet light. This color instability is also true of all available acrylic resin dental materials and those using a tertiary amine activator.

In accordance with the present invention the dentist will add to the system regardless of the package format, i.e., a paste-liquid or paste-paste, uncoated particles of muscovite mica in the size range of 1–50 microns in combination with zirconium dioxide, titanium dioxide or bismuth oxychloride coated muscovite mica particles in the same size range. Alternatively the dentist may employ only particles coated mica in the 1–50 micron size range preferably $TiO_2$ coated mica. By the judicious selection of particles sizes, as the following examples will exemplify as well as a ratio selection of coating to mica by weight, any desired hue shade and lustre may be formulated. Moreover, it has been discovered that the incorporation of such particles eliminate the need for ultraviolet inhibitors and absorbers in that the dental material surprisingly becomes color stable. It is postulated that the mica reflects the ultraviolet preventing color instability. The concentration of mica particles may vary for direct dental fillings and restorations from one to 20% with about 4% being preferred. The practice of the invention is further illustrated by the following examples:

EXAMPLE 1

FILLED TOOTH PAINT-ON FOR DENTAL COSMETIC APPLICATION

A mixture of 10cc of powder was treated with Tris (2-methoxyethoxy) vinyl silane as a coupling agent catalyzed with Sodium Hydroxide. The powder mixture consisted of:

4.33cc Fumed Colloidal Silica-7 milli micron size
1.66cc Fumed Colloidal Silica-12 milli micron size
1.66cc $TiO_2$ coated Muscovite Mica in a 35:65 wt. ratio and 10–35 micron size
1.44cc $TiO_2$ coated Muscovite Mica in a 26:74 wt. ratio and 10–35 micron size
1.44cc Muscovite Mica uncoated 10–35 micron size The above powder mixture was added in a proportion of approximately 20% by volume to Part A of a thinned two part unfilled BIS-GMA resin system. Part A of the system comprises BIS-GMA resin, tri-ethylene glycol dimethacrylate and N,N-dimethyl-para-toluidine whereas Part B comprises BIS-GMA resin, tri-ethylene glycol dimethacrylate and benzoyl perioxide. Part A was mixed to a relatively thick consistency with the powder mixture well dispersed. Part B of the resin system was thereafter added by equal volume to Part A. The resulting dental material was coated onto a tooth using a paint brush following conventional enamel surface preparation of the tooth by acid etching with 37% phosphoric acid. Acid etching is a conventional procedure used to obtain a mechanical retention between the applied dental material and tooth enamel. The above mixture approximately a "NEW HUE" shade #64. NEW HUE is a Registered Trademark of Dentsply Inc. York, PA.

EXAMPLE 2

FILLED TOOTH PAINT-ON FOR DENTAL COSMETIC APPLICATION $TiO_2$ coated Muscovite Mica in a powder mixture with Fumed Colloidal Silica were added to Part A of the thinned BIS-BMA resin system as described heretofore in Example 1 and in the same proportion, i.e., approximately 20% by volume to Part A. The total powder mixture of 10cc was treated as in Example 1 and consisted of:
- 3cc Fumed Colloidal Silica-7 milli micron size
- 2cc Fumed Colloidal Silica-12 milli micron size
- 3cc $TiO_2$ coated Muscovite Mica in a 35:65 wt. ratio and 10-35 micron size
- 2cc $TiO_2$ coated Muscovite Mica in a 26:74 wt. ratio and 10-35 micron size The above powder when added to the described resin system of Example 1 and then mixed with Part B approximates a "NEW HUE" shade of #62.

EXAMPLE 3
UNFILLED TOOTH PAINT-ON FOR DENTAL COSMETIC APPLICATION

A 5cc mixture of $TiO_2$ coated Muscovite Mica particles as identified in Example 2 but without Fumed Colloidal Silica was added in a proportion of 20% by volume to Part A of the thinned BIS-GMA resin system described in Example 1. The above material was used to cover slight tooth blemishes such as that caused from pulpal removal. This mixture enhanced the hue of the tooth and restored its lustre to that of the surrounding teeth.

EXAMPLE 4
DIRECT FILLING MATERIAL

A mixture of coated and uncoated Muscovite Mica particles treated with a coupling agent as described in Example 1, was added in a 4% total volume proportion to a filled BIS-GMA paste-paste resin system as described in the aforementioned U.S. Pat. No. 3,926,906 which is presently marketed under the Tradename "ADAPTIC", a registered trademark of the Johnson & Johnson Corporation of New Jersey in the universal shade formula. The Part A package of this dental filling material is distinguished from the Part B package in that Part A includes the activator whereas Part B includes the peroxide catalyst. Otherwise each package is substantially equal comprising a BIS-GMA monomer, a diluent and filler particles. A total mixture from Part A and Part B of 20cc was prepared in combination with mica particles as follows:
- 9.2cc Universal shade Adaptic Paste Part A Package
- .8cc Various Muscovite Micas added in the following ratios:
  - .5 parts $TiO_2$ coated Muscovite Mica in a 35:65 wt. ratio and 10-35 micron size
  - .4 parts $TiO_2$ coated Muscovite Mica in a 26:74 wt. ratio and 10-35 micron size
  - .1 part Muscovite Mica uncoated 10-±micron size
- 10cc Universal shade Adaptic Paste Part B Package After the above is adequately mixed the cured mixture approximates a "BIOFORM" shade #54. BIOFORM is a Registered Trademark of Dentsply Inc. York, PA.

EXAMPLE 5
DIRECT FILLING MATERIAL

Similar to Example 4 using a total sample mixture of 20cc consisting of:
- 8cc Universal Shade Adaptic Paste Part A Package
- 2cc Muscovite Micas added in the following ratios:
  - .5 parts $TiO_2$ coated Muscovite Mica in a 35:65 wt. ratio and 10-35 micron size
  - .166 parts $TiO_2$ coated Muscovite Mica in a 26:74 wt. ratio and 10-35 micron size
  - .166 parts Muscovite Mica uncoated 10-35 micron size
  - .166 parts Muscovite Mica uncoated 5-40 micron size
- 10cc Universal shade Adaptic Paste Part B Package After the above is properly mixed the cured resin approximates a BIOFORM shade #91. 91. The increased volume proportion of mica particles shifted the hue from one end of the BIOFORM shade guide to the other end.

EXAMPLE 6
DIRECT FILLING MATERIAL

.8cc of Muscovite Mica particles in the following proportion:
- .5 parts to $TiO_2$ coated mica in a 35:65 micron size.
- .4 parts $TiO_2$ coated mica in a 26:74 wt. ratio and 10-35 micron size
- .1 part uncoated mica 10-35 micron size was added to a powder Part A mixture of 9.2cc substantially of fused silica, fine enough to pass through a 325 sieve, which was treated with an aqueous solution of tris(2-methoxy ethoxy) vinyl silane catalyzed with sodium hydroxide and including about 1-2% of benzoyle peroxide;

A liquid Part B was prepared comprising 10cc of BIS-GMA resin monomer with less than 20tri-ethylene glycol dimethacrylate and about 1-2% N,N-dimethyl-para-toluidene.

The mixture of Part A to Part B produced a BIOFORM shade #54. Furthermore, the material passes the color stability test (4.3.6) of Specification #12 for Denture Base Resins of the Specifications of the American Dental Association Council on Dental Materials and Devices. Where the Part A mixture was increased to 10cc omitting the mica particles and then mixed with Part B the cured resin material failed the same color stability test.

EXAMPLE 7
TRANSLUCENT DENTAL ACRYLIC POLYMER FOR JACKETS, CROWNS, FALSE TEETH AND OTHER DENTAL APPLICATIONS (COLD CURE)

- 7.5cc Clear Methyl Methacrylate Polymer (powder) catalyzed with Benzoyl Peroxide
- .5cc Muscovite Mica in the following ratios:
  - .55 parts $TiO_2$ coated Muscovite Mica in a wt. ratio of 35:65 and a 10-35 micron size
  - .150 parts $TiO_2$ coated Muscovite Mica in a wt. ratio of 26:74 and a 10-35 micron size
  - .150 parts Muscovite Mica uncoated 10-35 micron size
  - .150 parts Muscovite Mica uncoated 5-40 micron size After the above is mixed with the appropriate amount of methyl methacrylate monomer (liquid) activated with N,N-dimethyl-para-toluidine, the cured resin system approximates a translucent BIOFORM shade #51.

EXAMPLE 8

TRANSLUCENT DENTAL ACRYLIC POLYMER FOR JACKETS, CROWNS, FALSE TEETH AND OTHER DENTAL APPLICATIONS (HEAT CURE)

A powder mixture of the following is prepared:
7.5cc Clear Methyl Methacrylate Polymer (powder)
5cc Muscovite Mica in the following ratios:
 .75 parts $TiO_2$ coated Muscovite Mica in a wt. ratio of 35:65 and 10-35 micron size
 .0835 parts $TiO_2$ coated Muscovite Mica in a wt. ratio of 26:74 and 10-35 micron size
 0.0835 parts Muscovite Mica uncoated 10-35 micron size
 .0835 parts Muscovite Mica uncoated 5-40 micron size After the above is mixed with an appropriate amount of methyl methacrylate monomer (liquid), the cured resin approximates a BIOFORM shade #59 and has translucency. Curing occurs by heat treating the mixed resin in an oven at 165° F for 9 hours.

EXAMPLE 9

FILLED TOOTH PAINT-ON FOR DENTAL COSMETIC APPLICATION

Uncoated and $TiO_2$ coated muscovite mica and Fumed Colloidal Silica were added to a resin of Ethyl 2-Cyanoacrylate. The purpose of this mixture is to cover unsightly tooth blemishes such as tetracycline stains and other gross tooth blemishes. The following 10cc of powder was mixed in the following amounts:
 3.33cc Fumed Colloidal Silica-7 milli micron size
 1.66cc Fumed Colloidal Silica-12 milli micron size
 1.66cc $TiO_2$ coated Muscovite Mica in a wt. ratio of 35:65 and 10-35 micron size
 1.14cc $TiO_2$ coated Muscovite Mica in a wt. ratio of 26:74 and 10-35 micron size
 1.14cc Muscovite Mica uncoated 10-35 micron size
 1.14cc Muscovite Mica uncoated 5-40 micron size The above powder is added by 20% by volume to Ethyl 2-cyanoacrylate resin which is slightly inhibited with dimethyl formaldihyde and activated with a mild tertiary amine such as methyl-para-toluidine in an organic solvent. The mixture is painted onto a tooth using a paint brush after the tooth enamel surface has been acid etched with 37% phosphoric acid to obtain mechanical retention for the matrix resin. The cured resin approximates a "NEW HUE" shade of #64.

EXAMPLE 10

FILLED TOOH PAINT-ON FOR DENTAL COSMETIC APPLICATION

Muscovite Mica coated with $TiO_2$ alone and Fumed Colloidal Silica were added to a resin system as described in Example 9. The total powder mixture of 10cc consisted of:
 3cc Fumed Colloidal Silica-7 milli micron size
 2cc Fumed Colloidal Silica-12 milli micron size
 3cc $TiO_2$ coated Muscovite Mica in a wt. ratio of 35:65 and 10-35 micron size
 2cc $TiO_2$ coated Muscovite Mica in a wt. ratio of 26:74 and 10-35 micron size The above mixture when added by 20% volume to the resin system as described in Example 9 approximates a "NEW HUE" shade #62.

EXAMPLE 11

UNFILLED TOOTH PAINT-ON FOR DENTAL COSMETIC APPLICATION

The same Muscovite Mica as described in Example 10 without Fumed Colloidal Silical was added to a resin system as described in Example 9 by 20% by volume. The above mixture was used to cover slight tooth blemishes such as that caused from pulpal removal. This mixture enhanced the tooth Hue and increased the lustre to that of surrounding teeth.

EXAMPLE 12

DENTAL MATERIAL FOR FACING OR REPAIR

Using clear methyl methacrylate polymer and various muscovite mica particles the powder mixture as described in Example 8 is formulated for use with a cyanoacrylate resin system as described in Example 9 for the purpose of repairing dental restorations such as Jackets, Crowns and False Teeth. The powder is mixed with the cyanoacrylate resin system in a ratio of 75% powder by weight to 25% ethyl 2-cyanoacrylate. This approximates a "BIOFORM" shade of #59 with translucency

EXAMPLE 13

COMPARATIVE FIELD LUMINANCE BETWEEN DIRECT FILLING MATERIALS

Three samples were tested for Field Luminance.

Sample A was a natural extracted tooth which was recently extracted and properly preserved in an aqueous solution of water ($H_2O$) and hydrogen perioxide ($H_2O_2$). The tooth when matched in shade with a "NEW HUE" shade guide approximated a shade of #64.

Sample B is the filled BIS-GMA paste-paste resin system as described in U.S. Pat. No. 3,926,906 and as marketed in the Universal shade by Johnson & Johnson under the Tradename "ADAPTIC".

Sample C is the formulation of Example 4. A Nikkon microscope Model #67446 was used to test the field luminance using a Nikkon light source with unfiltered light and with the transformer set at 7 volts and with the aperture of the light source ¼ closed. The microscope was focused on the various samples with the naked eye at 400X using a 40X objective and 10X occular. A Gossen, Luna Pro model Light meter with light meter microscope adaptor was used to record the degree of reflected light. The 10X occular was removed after establishing focus at 400X. The light meter was thus recording at 40X on the various samples. The light source was aimed through the objective in order to receive reflective light.

Samples B and C were prepared by mixing the Parts A and B together into a clear acrylic viewing block in a thickness of 6mm with a hole of a diameter of 4mm. Both samples B and C were permitted to cure. After curing both samples B and C were finely ground to remove any surface resin and to expose the filler particles present in the composite structure. The following are the results of this study:

Natural Tooth Sample A recorded an average meter reading of 6 on the light meter for one minute. This corresponds to 2383 Field Luminance in Foot Lamberts;

Sample B recorded an average meter reading of 5.5 for 1 minute. This corresponds to 1689 Field Luminance in Foot Lamberts;

Sample C recorded an average meter reading of 5.75 for one minute. This corresponds to 2288 Field Luminance in Foot Lamberts or a 33% increase over Sample B.

In addition, Sample B failed the test for color stability (4.3.6) of Specification #12 of the American Dental Associations Council on Dental Materials and Devices while Sample C passed.

EXAMPLE 14

A COMPARISON OF A CLEAR POLYMERIZED METHYL METHACRYLATE AND ONE WITH THE ADDITION OF VARIOUS UNCOATED MUSCOVITE MICA

Sample A
Uncoated Muscovite Mica added
  6cc Clear Methyl Methacrylate Polymer (Powder) with Benzoyl Peroxide added as a catalyst
  1cc 5-40 micron size Muscovite Mica uncoated
  1cc 10-35 micron size Muscovite Mica uncoated
  1.25cc Methyl Methacrylate Monomer (liquid) with N,N-dimethyl-para-toluidine added as an activator Sample B
  6cc Clear Methyl Methacrylate Polymer (Powder) with Benzoyl Peroxide added as a catalyst
  1cc Methyl Methacrylate Monomer (liquid) with N,N-dimethyl-para-toluidine added as an activator

PART ONE
(REFLECTIVE LIGHT TEST)

Both samples A and B were separately mixed and poured onto individual glass slabs to a thickness of 1.5mm and permitted to cure. Upon curing each sample was removed from its glass slab. Samples A and B both had a glass smooth lower surface and a porous upper surface (the upper surface is the surface in contact with air during curing). The porous surface produced a milky appearance in both samples. The samples A and B were viewed and recorded with the equipment as described in Example 13. Both samples were viewed and recorded with the glass smooth surface facing the objective of the microscope. Sample A when subjected to the light meter recorded an average meter reading of 7.5 for 1 minute. This corresponds to 2978 Field Luminance in Foot Lamberts. Sample B recorded an average meter reading of 7.2 for 1 minute. This corresponds to 2858 Field Luminance in Foot Lamberts.

PART TWO (TRANSMITTED LIGHT TEST)

Samples A and B were then recorded using an unfiltered substage with the aperture fully opened and the transformer of the light source set at 7 volts. This permitted transmitted light to pass through samples A and B. Sample A had an average meter reading of 7.5 for 1 minute. This corresponds to 2978 Field Luminance in Foot Lamberts. Sample B had an average meter reading of 7.85 over 1 minute. This corresponds to 3251 Field Luminance in Foot Lamberts.

PART THREE
(VISUAL TEST)

When viewed with the naked eye at 400X with transmitted light it was noted that Sample A had much fuzzier edges than that of Sample B. It was also noted that the mica particles measured 20 microns average and reflected a yellowish hue.

OBSERVATIONS

Sample A possessed a yellow milkyness (as previously described) transparent shade approximating "NEW HUE" #60. Sample B had a clear milkyness. With the addition of Muscovite Mica uncoated the Muscovite Mica limited the transmitted transparency of the clear methyl methacrylate. The internal diffusion of light caused by the muscovite mica particles within the clear methacrylate resin produced a yellow hue which is that found in natural teeth. What is claimed is:

1. A dental material comprising in combination; a polymerizable resin binder wherein said binder is at least one acrylic monomer, an agent for polymerizing said binder, an inorganic filler and an additive for controlling the hue and lustre of said material, said additive comprising finely divided particles of translucent muscovite mica in a concentration of between about 1 to about 20% by weight of said material.

2. A dental material as defined in claim 1 wherein said mica particles are within a size range of between about 1 to about 50 microns.

3. A dental material as defined in claim 2 wherein a predetermined proportion of said mica particles of up to 100% are coated with a material selected from the group consisting of titanium dioxide, bismuth oxychloride and zirconium dioxide.

4. A dental material as defined in claim 4 wherein said polymerizable binder is selected from the group consisting of: methacrylic esters, cyanoacrylates, 2,2-bis[4-3-methacryloxy-2-hydroxypropoxy)-phenyl]-propane (BIS-GMA) and the reaction product of N-phenylglycine and glycidyl methacrylate.

5. A dental material as defined in claim 5 wherein said inorganic filler is selected from the group consisting of silica, glass beads, aluminum oxide, fused silica, fused quartz and crystalline quartz.

6. A dental material as defined in claim 5 wherein said polymerizable binder comprises 2,2-bis[4-3-methacryloxy-2-hydroxypropoxy)-phenyl]propane (BIS-GMA) and wherein said mateial further comprises a reactive diluent; an activator and a peroxide catalyst.

7. A dental material as defined in claim 6 wherein said filler particles and said mica particles are treated with a organosilane keying agent.

8. A method for controlling the hue and lustre of a dental filling or restoration containing a polymerizable monomer composition wherein said monomer is at least one acrylic monomer including an inorganic filler as a portion of said composition comprising the step of; adding finely divided particles of transluclent muscovite mica to said composition in a range of between about 1 to 20% by weight of said composition.

9. A dental material as defined in claim 1 wherein said mica particles is in a concentration of between about 1 to 4% by weight of said material.

10. A method as defined in claim 8 wherein said mica is selected within a particle size range of from about 1 to about 50 microns.

11. A method as defined in claim 10 wherein a predetermined proportion of said particles of mica of up to 100% are coated with a material selected from the group consisting of titanium dioxide, bismuth oxychloride and zirconium dioxide.

12. A method as defined in claim 11 wherein the hue shade of said composition is controlled by varying the weight ratio of said titanium dioxide coating to said mica.

13. A method as defined in claim 11 wherein the hue shade of said composition is controlled by varying the particle size concentration of said additive within said size range.

14. A method for cosmetically treating the the surface of a tooth so as to establish a predetermined hue and lustre comprising forming a material composition containing a polymerizable resin binder wherein said binder is at least one acrylic monomer and an agent for polymerizing said binder, adding finely divided particles of muxcovite mica to said composition within a range of between about 1 to 30% by weight of said material composition and applying a thin film of said material composition to the surface of a tooth.

15. A method as claimed in claim 14 further comprising adding an inorganic filler selected from the group consisting of silica, glass beads, aluminum oxide, fused silica, fused quartz and crystalline quartz to said material composition.

16. A method as claimed in claim 15 wherein said particles of mica are coated with a material selected from the class consisting of titanium dioxide, zirconium dioxide and bismuth oxychloride.

17. A method as claimed in claim 16 wherein a predetermined proportion of said mica particles of up to 100% thereof are coated with titanium dioxide.

18. A method as claimed in claim 17 wherein the hue shade of said material composition is controlled by varying the weight ratio of said titanium dioxide coating to said mica.

19. A method as claimed in claim 17 wherein the hue shade of said material composition is controlled by varying the particle size concentration of said additive within said size range.

20. A method as defined in claim 14 wherein about 8% by weight of said additive is added to said material.

* * * * *